United States Patent [19]

Casey et al.

[11] Patent Number: 4,525,350
[45] Date of Patent: Jun. 25, 1985

[54] METHODS OF STIMULATING HOST DEFENSE SYSTEM WITH COENZYMES $Q_4$ TO $Q_{13}$

[75] Inventors: Adria C. Casey, Ridgefield; Alan D. Adler, West Redding, both of Conn.; Eugene T. Premuzic, Montauk, N.Y.

[73] Assignee: The New England Institute, Inc., Ridgefield, Conn.

[21] Appl. No.: 960,026

[22] Filed: Nov. 13, 1978

Related U.S. Application Data

[63] Continuation of Ser. No. 551,430, Feb. 20, 1975, which is a continuation of Ser. No. 343,487, Mar. 21, 1973, abandoned, which is a continuation of Ser. No. 95,026, Dec. 4, 1970, abandoned, which is a continuation-in-part of Ser. No. 757,862, Sep. 6, 1968, abandoned.

[51] Int. Cl.³ .................. A61K 37/48; A61K 31/12
[52] U.S. Cl. ........................... 424/94; 424/84; 424/88
[58] Field of Search ............. 424/85, 88, 94, 195, 424/331

[56] References Cited

U.S. PATENT DOCUMENTS

| | | | |
|---|---|---|---|
| 3,317,381 | 5/1967 | Umehara | 424/94 |
| 3,426,125 | 2/1969 | Shigeta | 424/94 |
| 3,452,144 | 6/1969 | Yamamura | 424/331 |
| 3,560,612 | 2/1971 | Matsumura | 424/94 |
| 4,056,613 | 11/1977 | Bertazzoli | 424/94 |
| 4,068,003 | 1/1978 | Miyata | 424/94 |
| 4,073,883 | 2/1978 | Yasuda | 424/94 |

FOREIGN PATENT DOCUMENTS

| | | | |
|---|---|---|---|
| 769791 | 3/1957 | United Kingdom | 424/94 |
| 925581 | 5/1963 | United Kingdom | 424/94 |

OTHER PUBLICATIONS

Burk, Radiation Res., Suppl., vol. 3, 1963, pp. 223, 230–231.
Chem. Abs., vol. 63, 1965, p. 980a.
Chem. Abs., vol. 64, 1966, p. 1158b.
Chem. Abs., vol. 67, 1967, Ab. No. 25401c.
Bliznokov (1), Int. J. of Cancer, vol. 3, 1968, pp. 336–343.
Bliznokov (2), Experientia, reprint, vol. 26, 1970, pp. 953–954.
Casy, Lipids, vol. 5, 1970, reprint, pp. 856–858.
Heller, Nature, vol. 199, Aug. 31, 1963, pp. 904–905.
Lemperle, J. Retic. Soc., vol. 3, Dec. 1966, reprint, pp. 385–397.
Ransom, J. Bacti., vol. 84, 1962, pp. 466–472.

*Primary Examiner*—Anna P. Fagelson
*Attorney, Agent, or Firm*—Pennie & Edmonds

[57] ABSTRACT

Method of controlling the host defense system in a body by internally administering coenzymes Q or carotenoids, and structurally related compounds at appropriate dosage schedules.

11 Claims, 15 Drawing Figures

% Increase in Hemolytic Antibody Titer Over Controls for Mice Stimulated With 150µgm/Mouse of Coenzyme Q10

Phagocytosis Stimulation by trans-Retinol

METHODS OF STIMULATING HOST DEFENSE SYSTEM WITH COENZYMES $Q_4$ TO $Q_{13}$

CROSS REFERENCE TO RELATED APPLICATION

This is a continuation of application Ser. No. 551,430, filed Feb. 20, 1975, which is a continuation of Ser. No. 343,487 filed Mar. 21, 1973, now abandoned, which is a continuation of Ser. No. 95,026, filed Dec. 4, 1970, now abandoned, and which is a continuation-in-part of Ser. No. 757,862, filed Sept. 6, 1968, now abandoned.

BACKGROUND OF INVENTION

Man and other animals have a complex system called the host defense system, or the reticuloendothelium system (RES) for resisting disease. For example, bacteria, parasites, virus particles, neoplastic cells, toxins, antigens, etc., are trapped and destroyed at one or more of the sites of this system. While there are many descriptions and schemes of classification for this system, one widely accepted morphological definition states that the principle components of the host defense system are:

1. The fixed macrophages which monitor the blood stream and are situated in the liver, spleen, bone marrow, and adrenal and pituitary glands;
2. The fixed macrophages which filter the lymph and are present in the sinusoids of lymph glands and follicles;
3. The free macrophages found characteristically in the serous cavities;
4. The fixed histiocytes of the connective tissues;
5. The monocytes of the blood;
6. The microglia of the central nervous system.

It is probable that the lymphocytes and plasma cells also should be included in this system since they certainly participate in recognized host defense functions.

The recognized general functions of this system are phagocytosis, intracellular destruction of alien matter, and antibody formation. To this list one can also add certain specific functions such as specific defense against hemovascular parasites, viruses, bacteria, fungi, tumors, etc.; resistance to shock of various types; hematopoiesis, red cell phagocytosis, and detoxification.

Clearly, if the functions of the host defense could be stimulated, then the host resistance to invasion might well be increased. However, it must be remembered that in some cases stimulation of only one function could have no overall beneficial effect or could even be detrimental. For instance, it is inefficacious to increase the rate of phagocytosis of a pathogen if at the same time greater or faster intracellular destruction cannot occur. Hence, while many substances, both synthetic and natural, can promote an increase in the rate of phagocytosis of invading organisms, few of them promote other host defense functions as well. Such materials have a limited clinical usefulness.

Reviews and articles on substances which stimulate or inhibit the host defense system or its individual subcomponent parts or functions are numerous. One of the earliest of such substances shown to have host defense activity is bacterial endotoxin. This has been the subject of numerous papers. Unfortunately, although it is stimulatory in small doses it is of course lethal in large doses. Before proceeding further it is useful therefore to list the ideal properties that a clinically useable host defense controlling substance should possess. In the case of either a stimulant or an inhibitor.

1. It should affect more than one function or component of the host defense;
2. it must not be toxic;
3. it must not be antigenic;
4. it must not be pyrogenic;
5. it must not cause hyperlasia;
6. it should act in a reasonably low dose;
7. it should produce no untoward side effects.

Many classes of compounds and natural products have been described by various workers as possessing stimulant effects on one or more of the host defense system functions. None of these known materials satisfy the complete criteria cited above for a stimulant or inhibitor useful as a therapeutic agent.

The eventual usefulness of an effective, nontoxic inhibitor of this system in lowering the rejection rate of transplanted organs and tissues may be almost as important as that of a useable stimulant material. The major problem in the post-surgical management of such transplant cases is to maintain the delicate balance in the patient's system between preventing the onset of serious infectious disease and not initiating rejection of the transplanted organ by the host defense system. As present, toxic drugs and/or heavy doses of ionizing radiation are needed to suppress the host defense to prevent transplant rejection. These may cause permanent impairment of the system, resulting in continuing high susceptibility to infectious diseases and, perhaps to neoplastic disease as well. Consequently, transplants of major organs will continue to be a highly hazardous and extremely expensive operation until such time as a nontoxic method of controlling host resistance can be developed for human use.

SUMMARY OF THE INVENTION

The invention is concerned with the use of a specific group of compounds for either stimulating or inhibiting and thus controlling the host defense system in animals and in man. These compounds are presently administered to the body intravenously, but other administrative modes including but not limited to intraperitoneal, subcutaneous, and intramuscular administration can be employed if desired as will be apparent to those skilled in the art.

Compounds found to be useful for controlling the host defense system include quinones, such as naphthoquinones and the ubiquinones. The naphthoquinones can contain side chains of various lengths, such as methyl naphthoquinone and vitamin K structures, for example, 2-methyl-3-phytyl naphthoquinone (K-1) which are host defense stimulants. Benzoquinone showed only a weak stimulating activity. The ubiquinones include the coenzymes Q, such as hexahydro coenzyme $Q_4$, through at least coenzyme $Q_{10}$. The particular chemical structure of the quinones can be varied so long as they retain the ability to control the host defense system to either inhibit or stimulate it.

Carotenoids and precursors, such as $\alpha$ and $\beta$-ionone, farnesol, trans-retinol, retinol palmitate, exhibited a host defense stimulating action while $\beta$-carotene, geraniol and geranyl valerate exhibited a host defense inhibiting action at the dosage levels and protocol employed. It is further to be expected that compounds of similar strucrture to those disclosed above will also be useful for controlling the host defense system.

The coenzymes Q generally exhibit an inhibitory effect at low dosage levels and a significant stimulatory effect at high dosage levels. The coenzymes that have been successfully tested to date include the hexahydro coenzyme $Q_4$, coenzymes $Q_6$, $Q_9$, and $Q_{10}$. The host defense activity of $Q_n$ increases as the numerical value increases and it is thus expected that the higher coenzymes, such as $Q_{12}$ and $Q_{13}$ will have increased activity. $Q_0$ showed no activity in phagocytosis and thus activity of the coenzymes below $Q_4$ is questionable but could readily be tested as set forth herein. A series of synthetic quinones, such as benzoquinone, has also shown only weak activity.

DESCRIPTION OF PREFERRED EMBODIMENTS

Preparation of Compounds for Testing

Each compound tested was injected intravenously in the tail vein as an emulsion prepared in 5 percent nonpyrogenic glucose solution or 0.9 percent non-pyrogenic sodium chloride (normal saline). The emulsifier used was either nonpyrogenic Ninol (lauric diethanolamide) or Tween 20 (polyoxyethylene sorbital monolaurate). The emulsions were prepared in a 500 ml Waring blender, kept in a water bath at 60° C. protected from light. Initial homogenization was for 45 seconds. The smaller doses were injected first and the emulsion was rehomogenized for 15 seconds before removing the next larger dose for injection. The method used to prepare the emulsions is important and has to be done exactly the same way to obtain reproducible results. Particle size was 2–5 microns and concentrations of test compounds in the emulsions ranged from 350 to 250 ug/cc. with 250 ug/cc. being the preferred concentration. The emulsions generally were used in the animal as soon as possible or while the emulsion was still fresh since the activity of the emulsion varies with time. For example, a noticeable decrease in activity of a test emulsion was observed after a period of just one hour while other emulsions increased slightly in activity initially, and later decreased in activity. The reasons for this variation in activity are not known but it is believed that the particular emulsifying agent used is at least partly responsible since different variations of the activity of the emulsions have been found when different emulsifying agents are used. Tween 20, for example, results in a fairly rapid decrease in activity while Ninol results at least partially in a slight increase in activity. Particle size is also believed to play a part in the activity variations of the emulsion.

Biological Evaluation of Compounds

The biological activity of host defense stimulants and inhibitors in animals and man is readily determined by one or more tests, one is a measure of phagocytic action and another a determination of stimulation of antibody synthesis. Phagocytosis is measured by the following test in which a specially prepared colloidal carbon is injected into rats and the rate of removal of the carbon from the blood stream is determined. Various other biological tests are employed including the key tests of increased survival time and survivorship when challenged by lethal dosages of disease-causing matter such as Friend virus leukemia in mice, dibenzpyrene induced tumors in mice, *Plasmodium Berghei* (malaria) in mice, *Salmonella Typhimurium* in mice and *Rous Sarcoma* in chickens.

Phagocytosis Activity

Colloidal carbon (Pelikan Ink, Gunther Wagner, Hanover, Germany) is centrifuged at 3300 rpm for 30 minutes in order to eliminate any large particles. This insures that particles above 0.5 micron are removed. After verifying the absence of larger particles microscopically, the supernatant is decanted off and dialyzed for 48 hours or longer until all traces of phenol have been removed. It is then diluted with pyrogen free distilled water to a concentration of 56.7 mg/ml of carbon based on a dry weight determination. Gelatin from a single master batch is then added to give a 1 percent solution and the solution kept above 30° for a few hours. The same batch of carbon (stored in small aliquots to maintain sterility) is used for each group of similar experiments. The colloid is warmed to 37° before injection. In a test for phagocytic activity of the host defense compounds, six to eight different doses of emulsified compound are given prior to determination of carbon clearance rates as shown in the accompanying drawings. Each host defense component was administered intraveneously forty-eight hours before challenge with the colloidal carbon.

Forty-eight hours later the gelatin-covered carbon colloids are injected in the amount of 28 and 35 mg. per 100 g. of rat into the femoral vein of the animal in the test animals as well as the control animals. Syringes are utilized with a rubber plunger and a $\frac{1}{2}''$ 27-gauge needle for intravenous injection of the heterodispersed carbon colloid. Only CFN adult males are used, weighing between 170 and 190 gm. Upon receipt all animals are placed in quarantine for one week. They are then transferred to temperature and humidity-controlled quarters designed to protect against microbial cross-contamination from other animals in other rooms.

In each experiment 7 to 10 experimental animals are used for each dose level administered and 7 to 10 controls are run. The control animals are injected with the identical material as the experimentals with the exception of the host defense compound being tested. Aliquots ($10\gamma$) of capillary tail blood from the tip of the tail are taken at five-minute intervals from each test rat in a straight bore pipette and delivered into 1.5 ml. of sodium carbonate.

Optical density of the carbon in the sodium carbonate is determined and plotted on a log-linear graph. The usual time it takes for 50 percent of the carbon to disappear from the control animals is of the order of 20–25 minutes. The average absolute deviation in clearance times for the 7 to 10 animals at each dose is less than 5 percent.

A number of compounds were tested according to the above procedure for phagocytic activity and the final results plotted as percent of control clearance time against weight dose of the emulsified test compound. Experimental data for several of the compounds is set forth in FIGS. 1, 2, 3, and 4 of the drawings, cf. figure legends.

For determination of stimulant or inhibitory effect on antibody synthesis, the standard procedure described by Kabat and Mayer (EXPERIMENTAL IMMUNOCHEMISTRY, Chas. C. Thomas, Publisher, Springfield, Ill., 1961) is used. The host defense compounds in emulsion form are intraveneously injected in mice. Two days later, the mice are injected with sheep red blood cells and then bled at suitable intervals. The hemolytic antibody titer of the sera obtained from the blood samples is then determined using the 50 percent end point method, calculating the best fitting regression line between probit percentage hemolysis and log serum dose.

Figure 2:
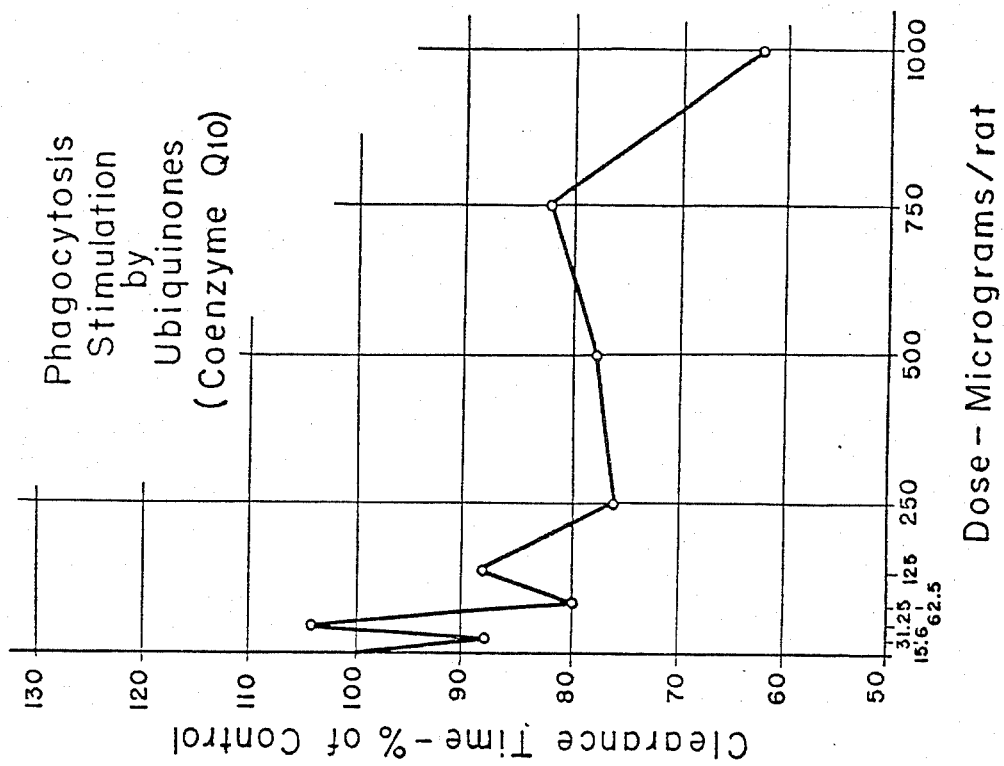
FIGS. 1 and 2 show the stimulatory activity of two ubiquinones, namely coenzyme $Q_6$ and coenzyme $Q_{10}$. The curves show the dose in micrograms per rat versus clearance time expressed as percent of control.
Figure 1:
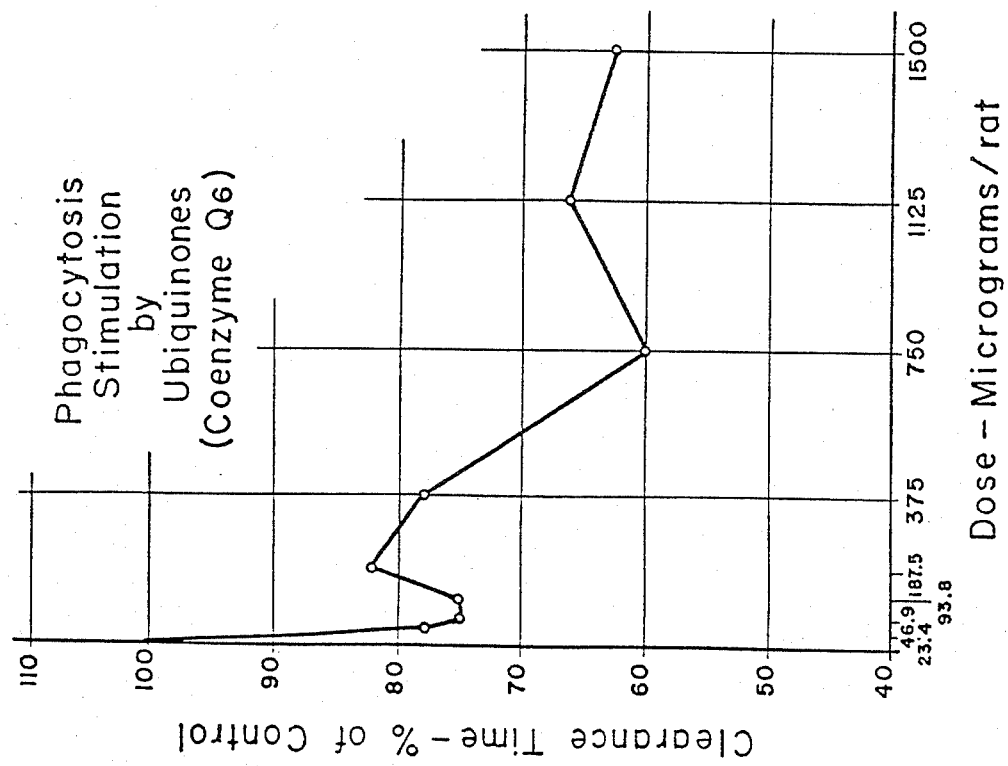
Figure 3:
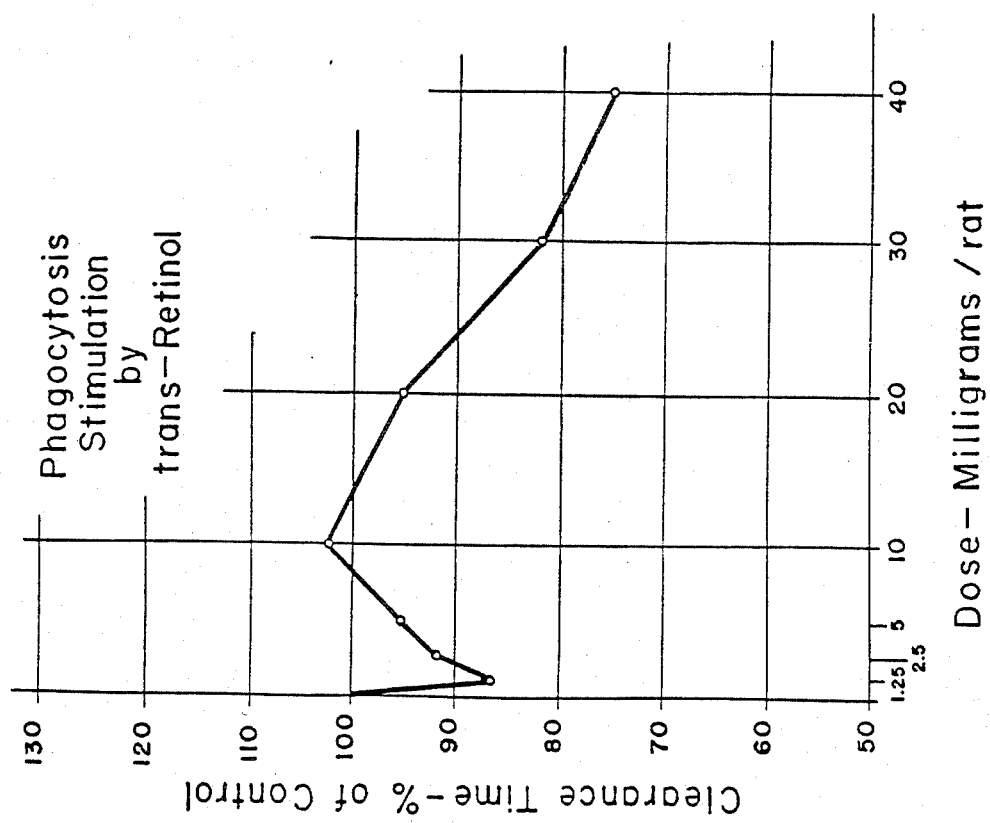
FIG. 3 shows representative clearance times as percent of control with varying doses in milligrams per rat for trans-retinol.

The time of the administration of the various host defense compounds shown in FIGS. 1 through 3 was constant, namely 48 hours prior to challenge in the phagocytosis tests.

Over the dosage ranges indicated in FIGS. 1 through 3, coenzymes $Q_6$ and $Q_{10}$ as well as trans-retinol were mainly stimulatory for the host defense system.

Figure 5:
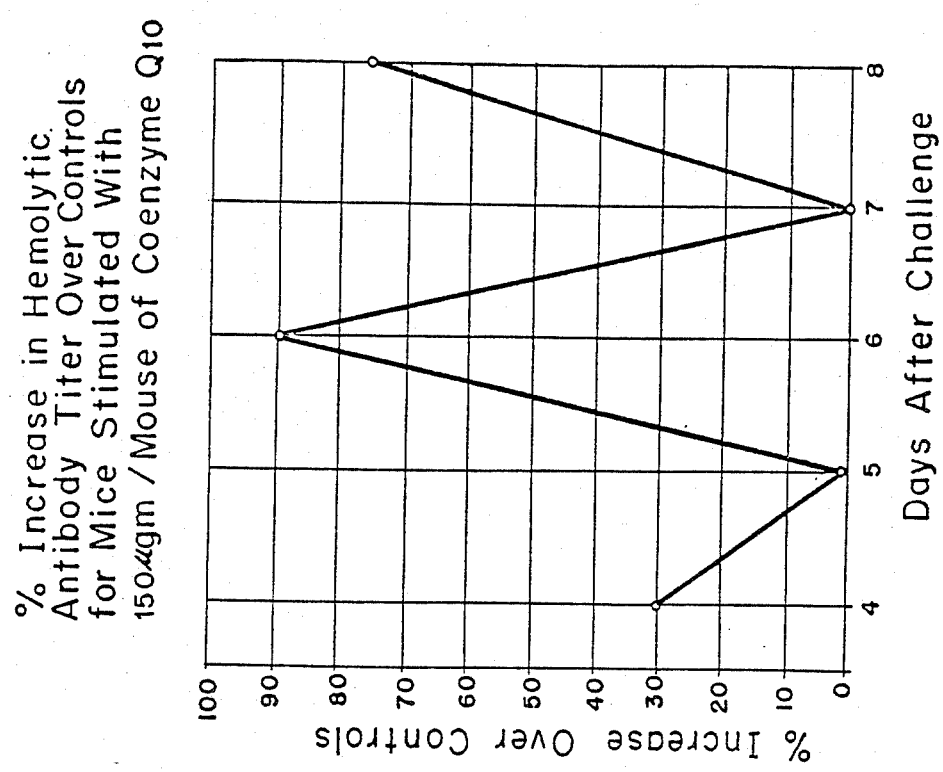
FIG. 5 is a graph showing the increase in hemolytic antibody titer of one of the compounds, namely coenzyme $Q_{10}$, injected intravenously into the mice, and which is representative of the other compounds used according to this invention.

The curve in FIG. 5 shows the percent increase in hemolytic antibody titer using a standard dosage of 150 micrograms per mouse. The host defense compound, coenzyme $Q_{10}$ was intraveneously injected into the mice in the emulsion form, as disclosed above, 48 hours prior to the injection of the sheep red blood cells and the blood samples taken 4, 5, 6, 7 and 8 days after administration of the sheep red blood cells.

It should be noted that any given compound can be stimulatory in a portion of its dose range and alternatively inhibitory in another portion of its dose range, using the same time of injection or dosage protocol. The degree of stimulatory and inhibitory action on the host defense system also varies with the dosage level as shown in FIGS. 1 through 3.

Figure 4:
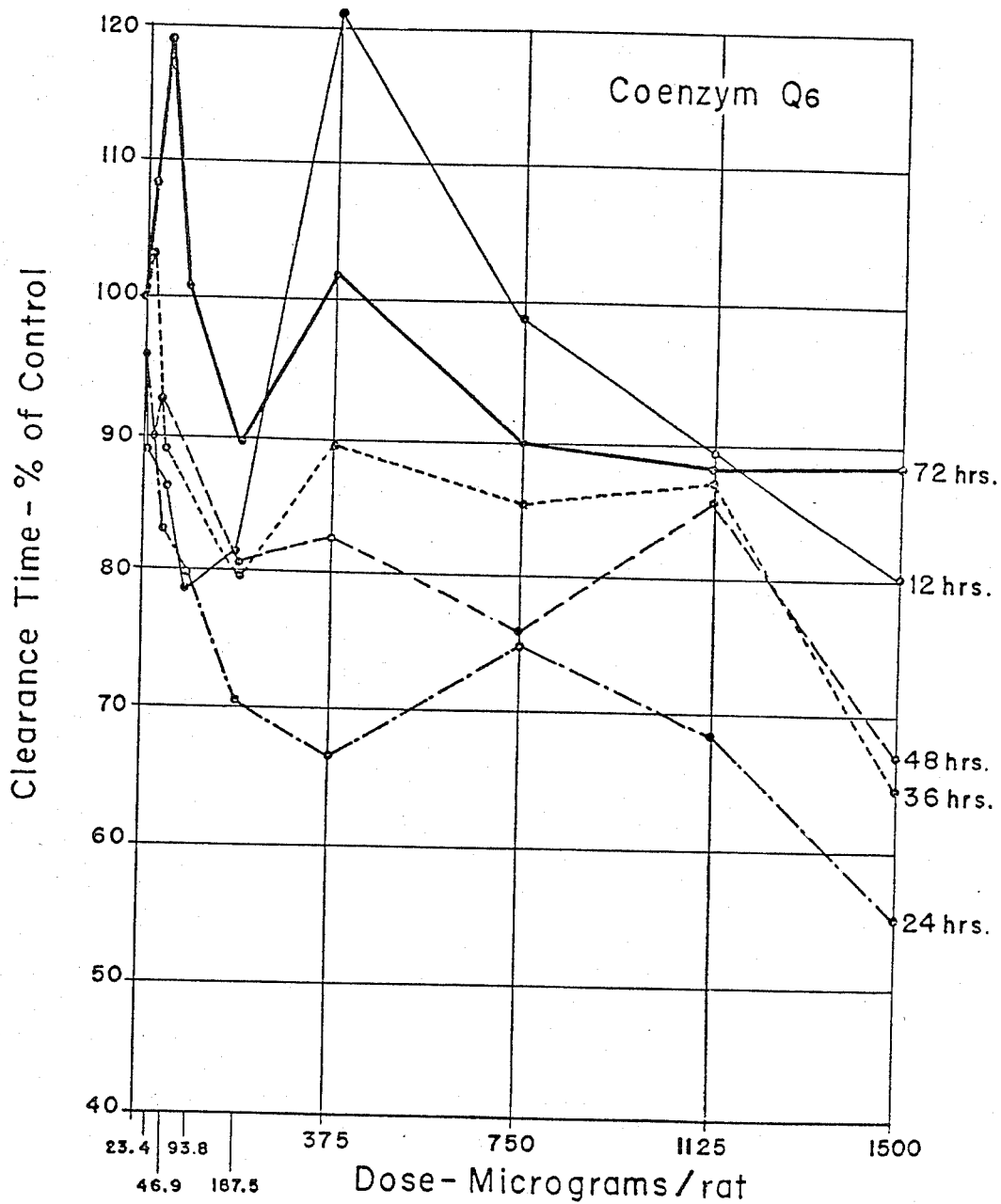
FIG. 4 shows the clearance time expressed as percent of control of coenzyme $Q_6$ in varying dosages and time in phagocytosis.
Figure 7:
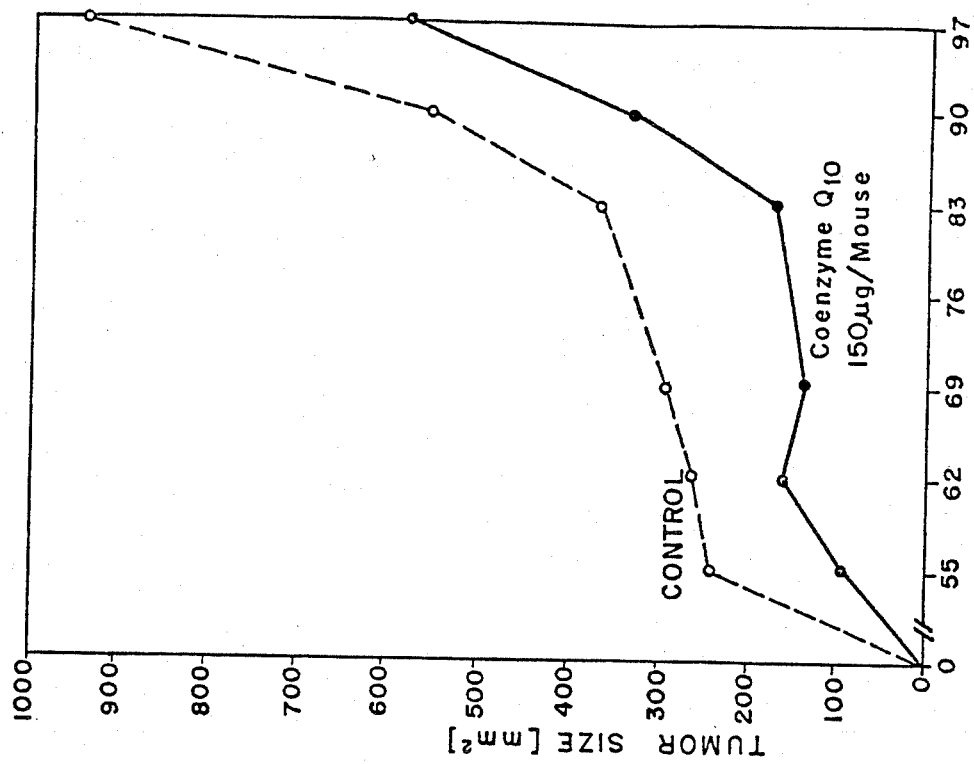
Figure 6:
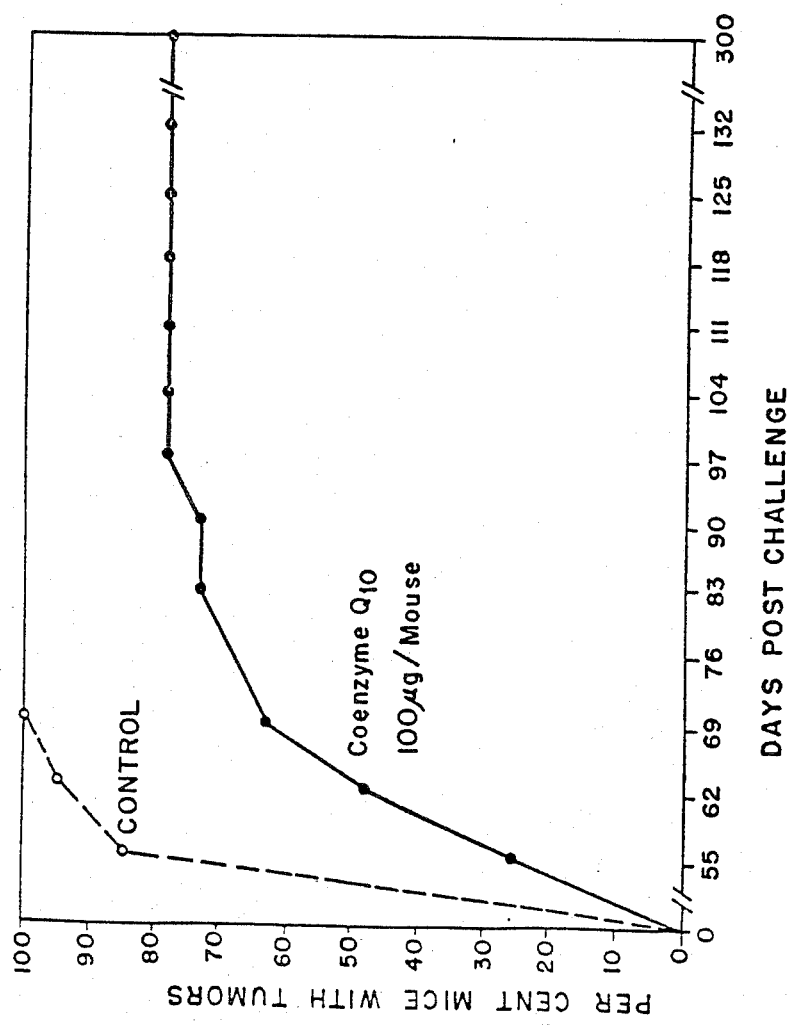
Figure 9:
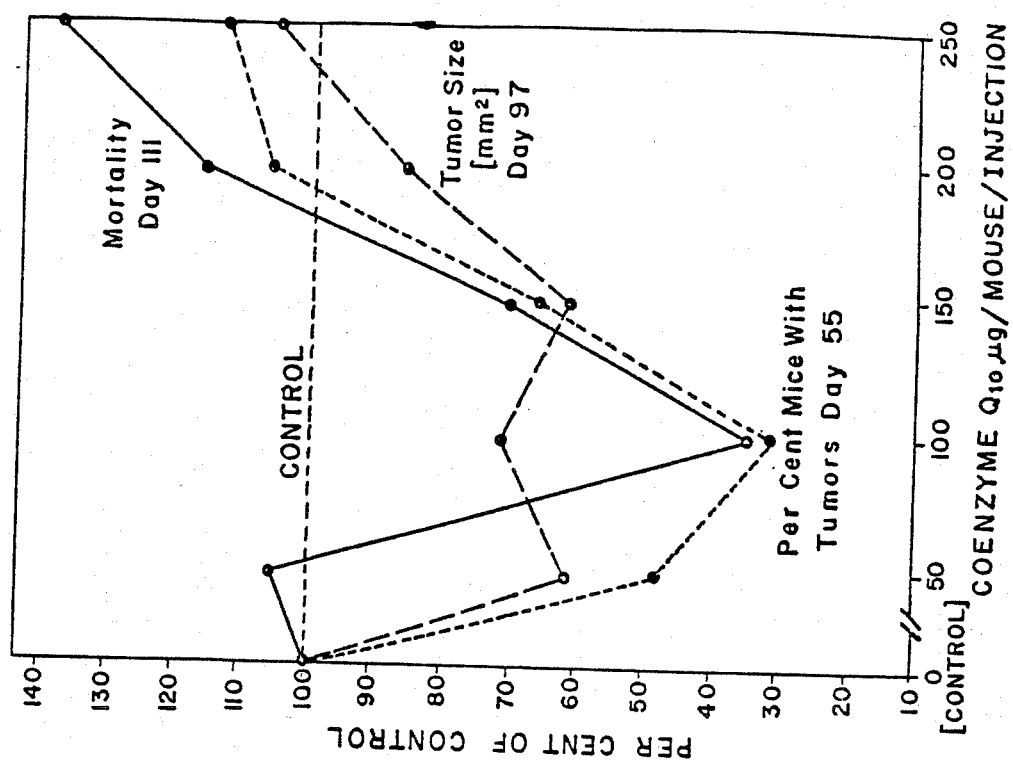
Figure 8:
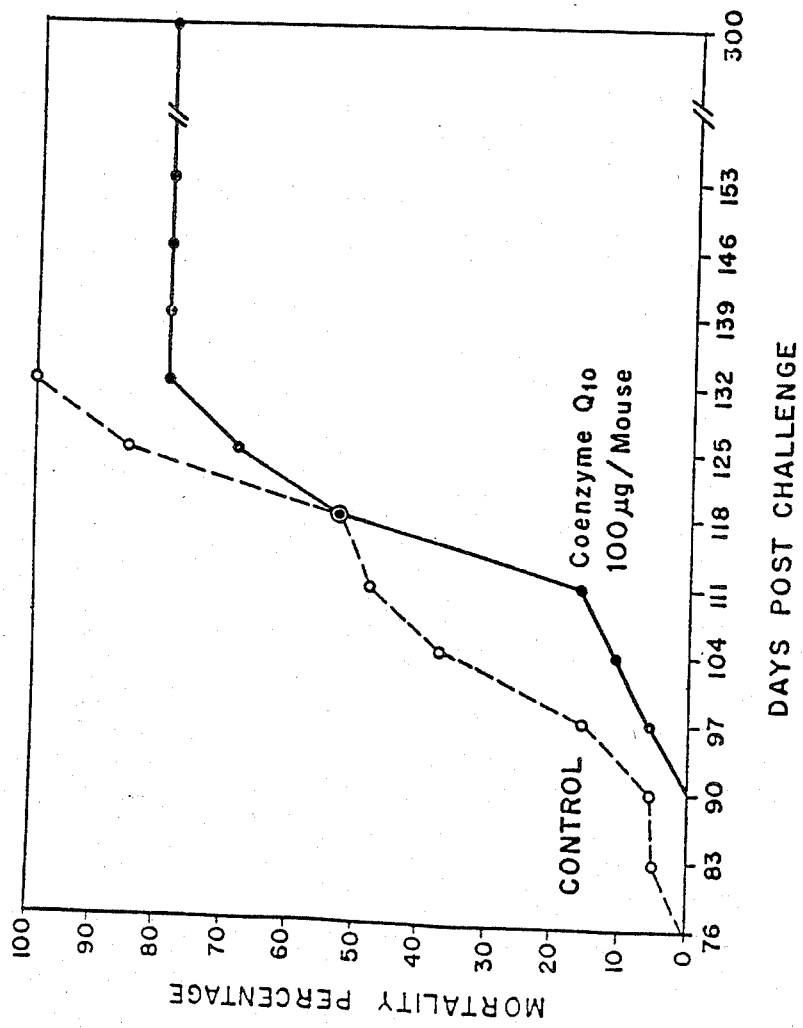

It should also be noted that the time of administration will modify the dose ranges which are inhibitory and which are stimulatory. The data shown in FIG. 4 illustrates this phenomena using coenzyme $Q_6$ as a representative compound for controlling the host defense system in the standard phagocytosis test described above. From these curves it can be seen that a dosage of 375 micrograms per rat, for example, given 24 hours before challenge in the phagocytosis test that coenzyme $Q_6$ showed a much higher activity for stimulating the host defense system than when the same dosage was given 12, 36, 48 and 76 hours before challenge. When the same dosage was given under the same conditions 12 hours before challenge, the same compound, coenzyme $Q_6$ showed considerable inhibitory action on the host defense system.

Thus in administering the compounds of this invention to control the host defense system, a properly selected dosage protocol should be used to control the host defense response on either a stimulatory or inhibitory basis as will be apparent to one skilled in the art. The dosage and dosage protocol selected by one skilled in the art will also depend upon whether the host defense compound is being used for the treatment of a disease already diagnosed or prophylatically.

The exact dose level will also be dependent on the particular host defense compound being used as well as the mode of administration. For example, trans-retinol, methyl naphthoquinone, and the vitamin K series, as well as the carotenoids and procursors are useful in the range of mg. per rat or animal and have exhibited significant activity when injected intravenously from about 20 to 40 mg. per rat. The coenzymes Q, however, exhibit pronounced host defense activity in the microgram range and are preferably injected into mice weighing approximately 20 gm. at about 150 micrograms. As a general rule, the coenzymes can be injected intravenously to stimulate the host defense system at about 7.5 milligrams per kilogram of body weight Other modes of administration, such as intramuscular or subcutaneous injection may generally require larger dose levels as will be apparent to those skilled in the art. Depending on the weight of the animal, the dose may be given over a period of time for example 1 to 4 doses a day which will total about 7.5 milligram/kilogram or which will total 30 milligrams per kilogram or approximately 0.45 grams for a body weight of 60 Kg.

Dibenzpyrene-Induced Tumors: 3,4,9,10-dibenzpyrene (DBP) was dissolved in peanut oil and 0.5 ml. was injected subcutaneously into the lateral abdominal wall of $C_{57}Bl_6$ mice. The concentration of the DBP was 2 mg/ml. In preliminary experiments it was established that this dose produced local tumors in 100 percent of the injected animals and mortality higher than 90 percent within eighteen to twenty weeks after administration. After treatment of injection of coenzyme $Q_{10}$ emulsion with dose and time schedules shown in FIGS. 6–9, the following parameters were followed:
1. Percent of mice developing tumors.
2. Changes in tumor size.
3. Percent of mortality.
4. Mean survival time.

Figure 10:
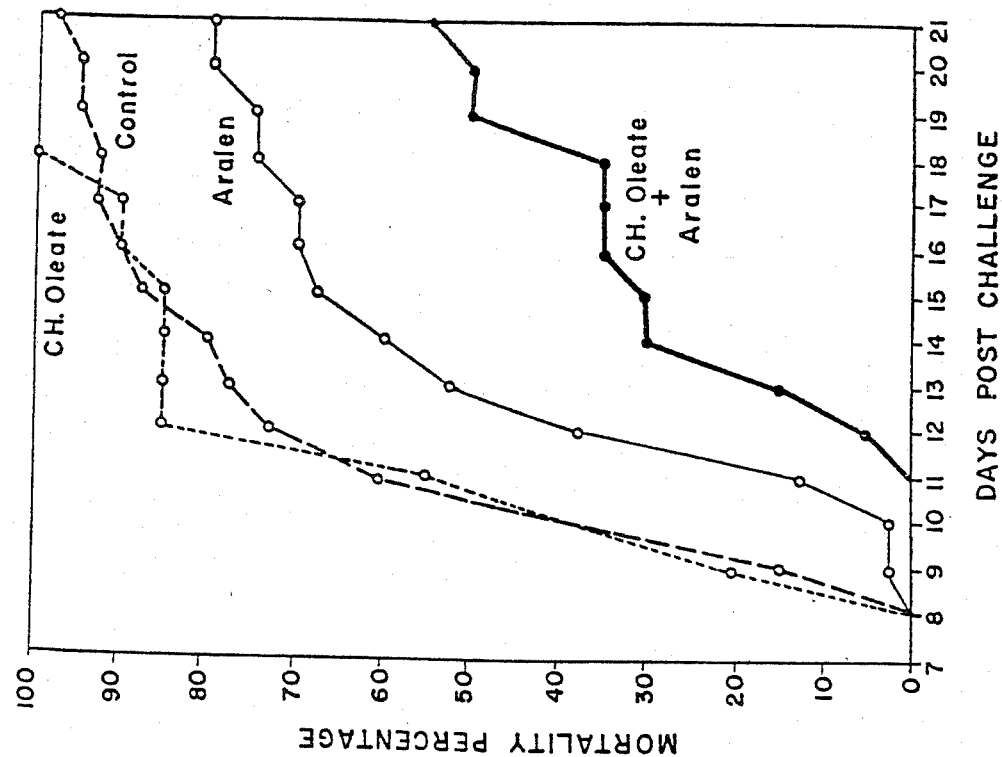
Figure 11:
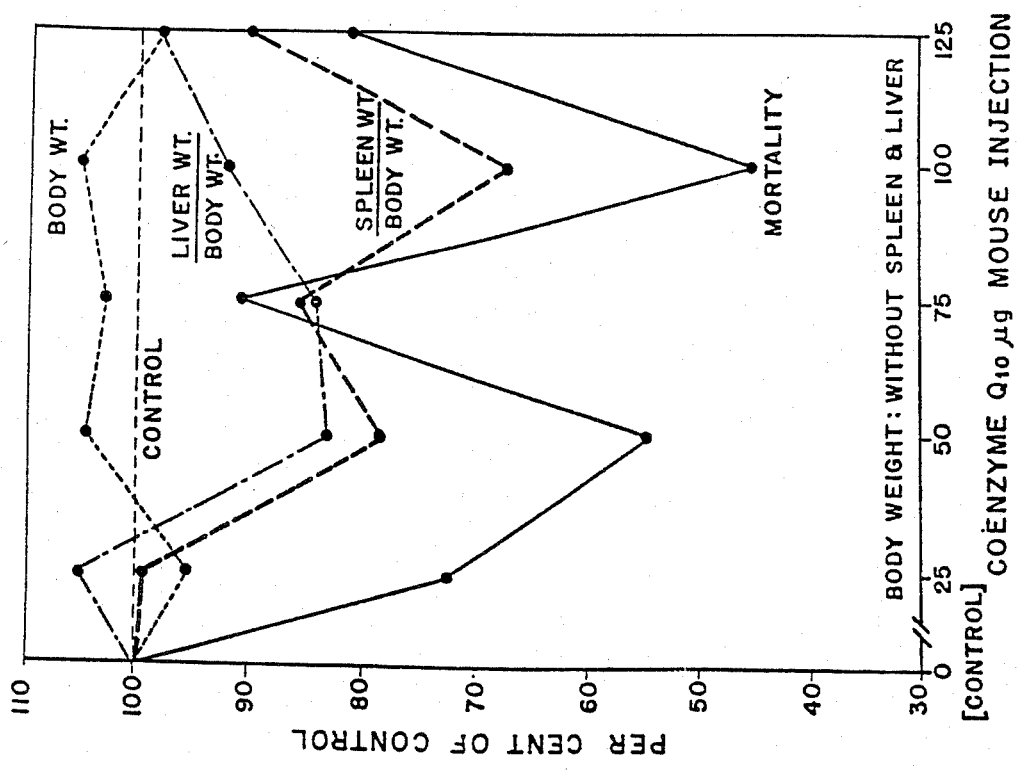
Figure 13:
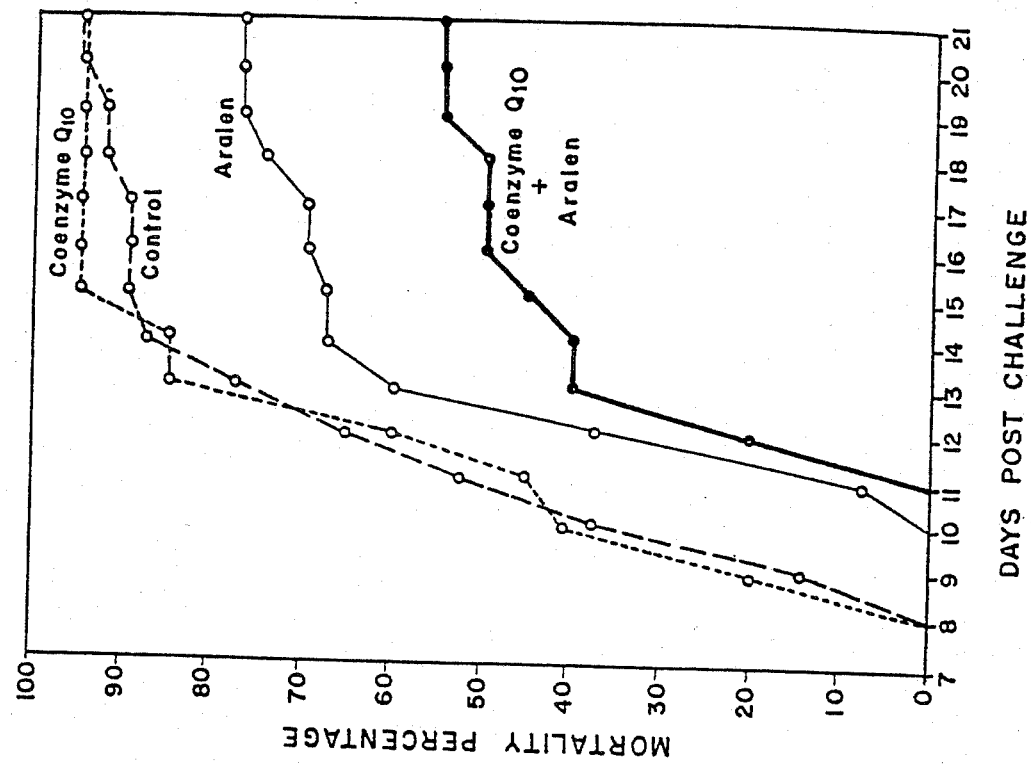
Figure 12:
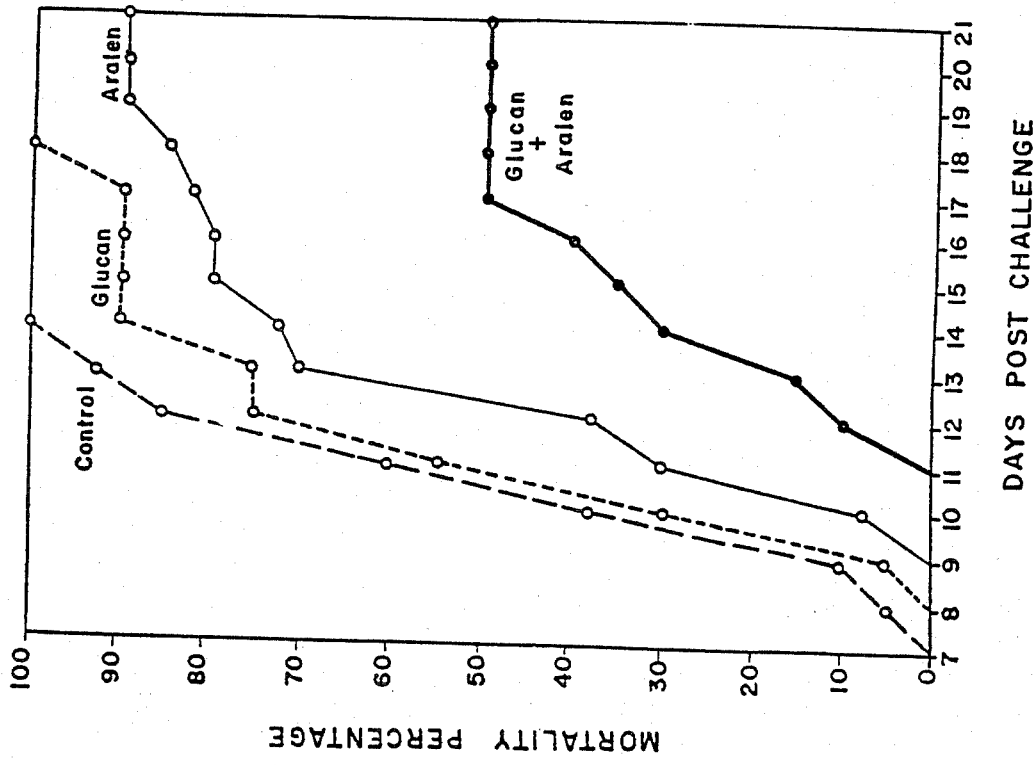
Figure 15:
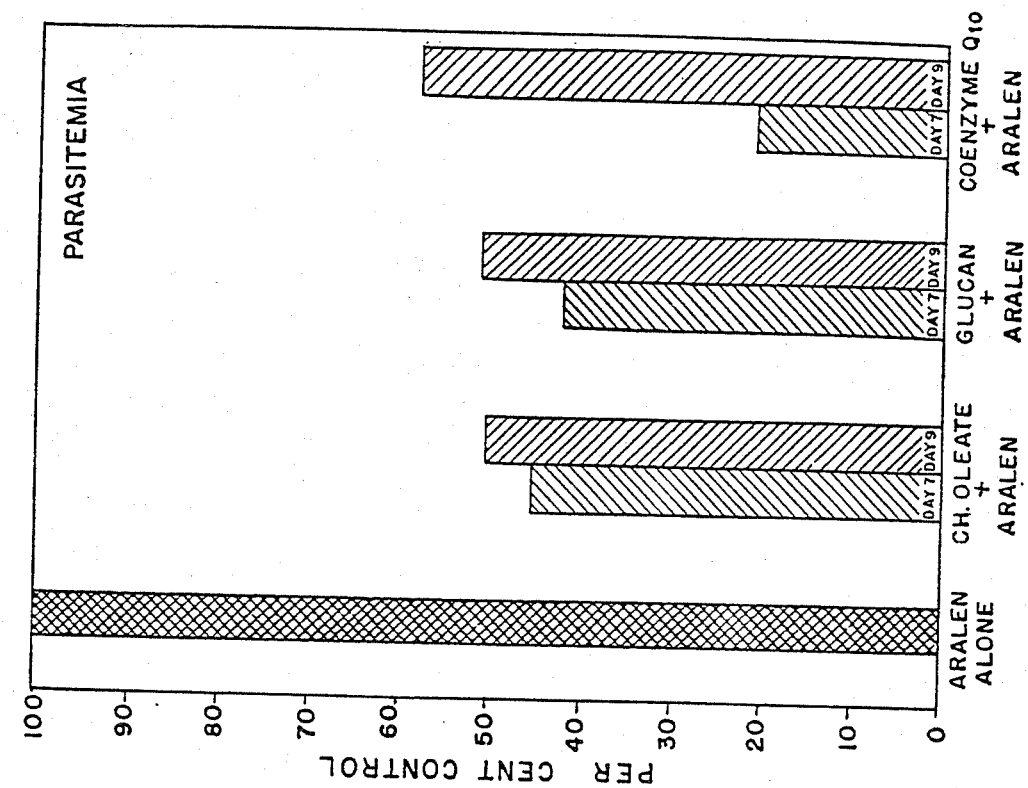
Figure 14:
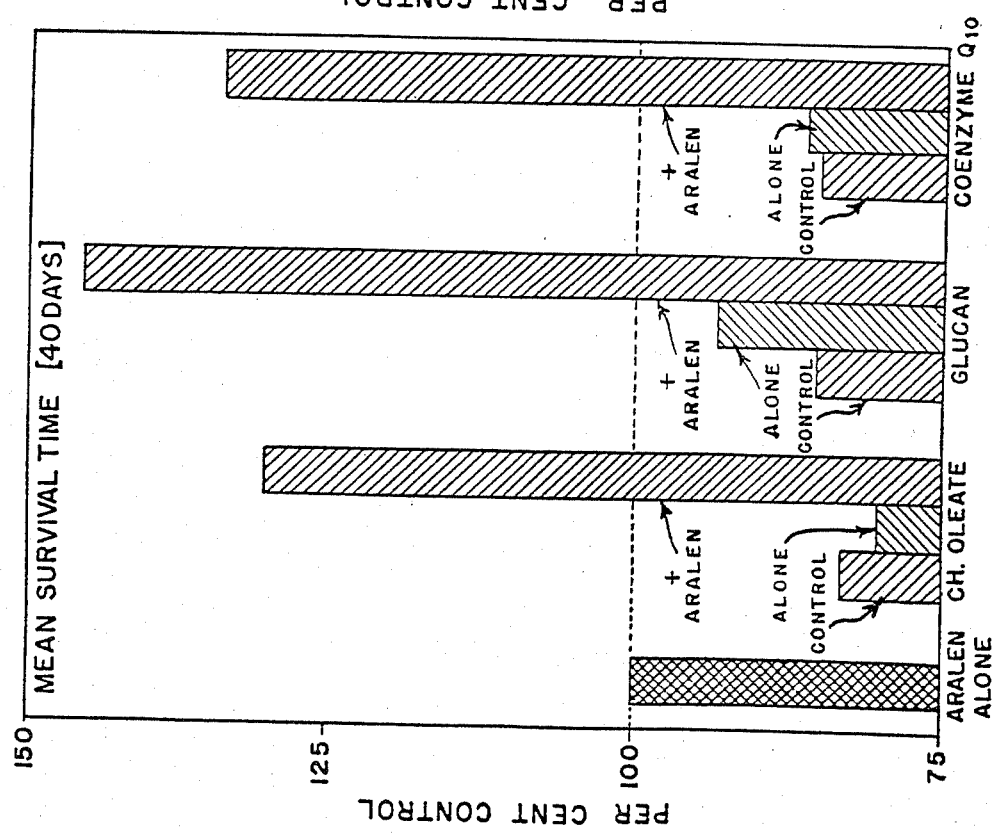

Friend Virus Leukemia: A large batch of Friend Virus (FV) was prepared and stored at $-60°$ C. Preliminary testing established that 0.2 ml. of this preparation, diluted 1:1000 and administered intravenously into Swiss Webster mice, produced splenomegaly (mean spleen weight more than 1000 mg. 20 days after challenge) and mortality higher than 90 percent. After treatment by injection of coenzyme $Q_{10}$ emulsion with dose and time schedules shown in FIG. 10 the following parameters were followed:
1. Changes in body weight 30 days after challenge.
2. Changes in spleen and liver weight 30 days after challenge.
3. Percent of mortality after 7 weeks.

Each mouse was given the dosage indicated four times 7, 14, 21 and 28 days after challenge and the above data were determined 30 days after challenge. The mortality was determined 7 weeks after challenge. All of the mice eventually died, probably of leukemia but this was not determined.

*Plasmodium Berghei* (malaria): Based on the assumption that the curative effect of antimalarial drugs is not only direct against the malarial parasites but requires also participation of the host defense or Reticuloendothelial System (RES) experiments were designed to demonstrate this relationship by using a combination of antimalarial drugs and RES-stimulating agents.

The antimalarial drug used was doses of Aralen (chloroquine hydrochloride) injected intramuscularly 2 hours before challenging the mice with *Pl. Berghei*. Stimulation of the RES was obtained by a single intraveneous injection of emulsions of cholesteryl (CH.) oleate or glucan, known RES-stimulating agents, or coenzyme $Q_{10}$.

The results are presented in FIGS. 11–15 and they demonstrate that stimulation of the RES by cholesteryl oleate or coenzyme $Q_{10}$ alone does not modify the course of rodent malaria, but a combination of RES stimulation and specific therapy (Aralen) results in increased survival time and increased survivorship. In addition, treatment with coenzyme $Q_{10}$ or cholesteryl oleate or glucan and Aralen results in reduced parasitemia. Neither of the combinations of cholesteryl oleate with Aralen or glucan with Aralen is a useful combination due to its undesirable side effects and toxicity. Coenzyme $Q_{10}$, alone or with Aralen, has shown no such undesirable side effects.

In these experiments the cholesteryl oleate was prepared containing 130 mg./ml. in a 5 percent glucose solution using Tween 20 as an emulsifying agent and was injected into the mice at a dose of 2 ml./mouse or 6 mg. of the CH oleate/mouse.

The glucan solution was prepared as a 1 mg./ml. solution in normal saline by boiling for about one hour and then emulsifying the glucan with Tween 20. This emulsion was injected into the mice at a dosage level of 0.4 ml./mouse or 400 μg./mouse.

The coenzyme $Q_{10}$ was prepared in the same manner as given above and was injected into the mice at a dosage level of 150 μg./mouse intravenously and alternatively at 500 μg./mouse intramuscularly.

The Aralen was prepared as a solution of normal saline at a concentration of 3.2 mg./ml. expressed as the base and administered to the mice intramuscularly at 320 μg./mouse.

In all cases cholesteryl oleate, glucan and the coenzyme $Q_{10}$ was administered to the animals 48 hours before challenge with *Plasmodium Berghei* and the Aralen 2 hours before challenge.

*Salmonella typhimurium:* All animals infected with a lethal dose of *Salmonella typhimurium* had a mortality rate of 100 percent within about three days. Mice treated with the appropriate dose of the compounds disclosed herein five days before challenge with the above bacteria have an increased survival time. Mice immunized with *Salmonella typhimurium* vaccine alone exhibit increased survival time and a mortality rate of approximately 80 percent. Immunized mice receiving the proper dosage (depending on the specific compound being employed) of the compounds described herein to stimulate the host defense system both before immunization (four days) and before challenge (five days) of the lethal dose of *Salmonella typhimurium* not only show a significant increase in survival time over any of the above treated animals but show the significant decrease in the mortality rate to approximately 40 percent. The dose of coenzyme $Q_{10}$ used was 150 micrograms per 20 gram mouse.

*Rous sarcoma* virus in chickens: To control and regress the tumors appropriate dosage levels in the range of 5 to 10 milligrams per kilogram were administered on the seventh and fourteenth day after challenge. These caused complete regression of the tumor in approximately 50 percent of the animals.

It has been demonstrated that coenzymes Q markedly increase phagocytosis and thus eliminate foreign invaders, stimulate antibody production, and increase survival time and decrease mortality in experimental infections and neoplasia. Coenzyme Q treatment by intravenous emulsion injection markedly decreases splenomegaly and hepatomegaly and increases survival time after challenge with Friend leukemia virus. In animals challenged by 3,4,9,10-dibenzpyrene subcutaneously to induce tumors, similar treatment by intravenous injection of coenzyme Q emulsions prolongs the latent period markedly, reduces the percentage of mice with tumors, increases survivorship and prolongs the survival time. Similar treatment with host defense stimulants, such as the coenzyme $Q_{10}$ alone does not modify the course of rodent malaria (*Plasmodium berghei*) but a combination of stimulant and a specific anti-malarial (such as Aralen) results in markedly increased survival time and survivorship and in reduced parasitemia.

The appropriate dosage and timing of administration of any particular compound to control the host defense system can be established by routine experimentation. It has also been found that the compounds used to control the host defense system can be used at specific dosages per body weight in different diseases to obtain similar results with respect to the stimulatory and inhibitory action of the host defense compounds.

The host defense compounds of this invention can also be administered and the dosage and dosage protocol determined by clinical response for each individual patient in the same manner as many other drugs are administered, such as cortisone.

The compounds used to control the host defense system described herein are useful and widely applicable alone or in combination with other means of treatment to stimulate the host defense system against attacks of diseases including bacteria, parasites, virus, fungi, tumors, resistance to shock of various types, as set forth herein. For example, the host defense compounds can be used to stimulate or inhibit the host defense system in animals and man for endotoxin shock, bacterial infection, such as *Salmonella typhimurium*, virus infections, such as vaccinia virus (cowpox), certain tumors such as Rous sarcoma in chickens, and Walker carbinoma, leukemia, trypanosomiasis, Ehrlich ascites carcinoma, and burn shock.

Applicants do not contend that the host defense compounds or emulsions of this invention alone or in combination with other modes of treatment are useful for treating or aiding in the prevention of all types of diseases broadly referred to above since insufficient data are available. The host defense compounds, however, have been found to be useful for treating or aiding in the prevention of all diseases which have been treated to date. However, since the host defense compounds of this invention stimulate the natural host defense mechanism of the body, it would be expected that the compounds would be effective and useful for treating or aiding in the prevention of any disease as normally or naturally combated by the natural host defense system.

These compounds can also be used as described above under proper dosage protocol to inhibit the host defense system. This effect should be valuable in the transplant of various organs in animals and man to aid in preventing rejection of the transplanted organ by the host defense system without encountering the dangers involved with other methods. Again the proper dosage protocol to obtain the desired degree of inhibitory action can be determined by those skilled in the art.

The compounds disclosed herein can be used alone in prophylaxis to keep the host defense system stimulated against various diseases as described above in the case of tumors induced by the chemical carcinogen, 3,4,9,10-dibenzpyrene. The compounds can be used in therapy to increase the level of resistance to various diseases as shown above in the treatment of Friend virus leukemia.

The compounds of this invention are also advantageous when used in conjunction with vaccines, antibiotics, antiparasitic agents, burn therapy, surgical and other known medical procedures to significantly aid in prophylaxis therapy of the various diseases described above. In a particular example, the combined treatment by emulsions of coenzyme $Q_{10}$ and Aralen significantly aid in increasing resistance to malaria.

The various vaccines, antibiotics, antiparasitic agents and other drugs that can be used in combination with the host defense compounds of this invention include those well known in the art and therefore need not be described specifically here in detail. When using the compounds as disclosed herein in combination with such other therapeutic agents, they can be administered prior to, together with, or after the administration of the therapeutic agent as can be determined by those skilled in the art to obtain the results desired.

The compounds in this invention can also be used in conjunction with conventional radiation treatment and radiomimetric chemicals.

In all of the experiments described herein with respect to mice and rats, the weight of the mice was approximately 20 grams and the weight of the rats approximately 180 grams so that the dosages per weight of the animal was sufficiently constant so as not to introduce any variable of statistical significance.

The preparations of this invention used to control the host defense system were tested for pyrogenic activity by standard tests from the U.S. Pharmocopeia, 17th revision, 1965, by intravenous injection in emulsion form as described above into male New Zealand rabbits. The animals were observed for temperature rise and no pyrogenic activity was found.

All of the compounds disclosed herein as active in controlling the host defense system under proper dosage protocol are well-known compounds and their methods of manufacture also are well known and therefore further details concerning their chemical and physical properties and manufacture methods is not necessary.

We claim:

1. The method of enhancing a body's resistance to disease which comprises stimulating the host defense system of the body by administering an effective amount of a compound selected from substantially pure coenzymes $Q_4$ to $Q_{13}$ or mixtures thereof.

2. The method of claim 1 in which the compounds are administered in the form of a solution or an emulsion.

3. The method of claim 1 in which the compound or compounds are administered as a prophylactic.

4. The method of claim 3 in which the compounds are administered in combination with a vaccine.

5. The method of claim 1 in which the compounds are administered in combination with a therapeutic preparation.

6. The method of claim 5 in which the therapeutic preparation is a member of the group selected from an antibiotic, an antiparasitic agent, antihistamine or a radiomimetric chemical.

7. The method of claim 1 in which the compounds are administered in combination with physicochemical therapy.

8. The method of claim 7 in which the physicochemical therapy is burn therapy and radiation therapy.

9. The method of reducing tumoral growth in an animal body which previously acquired tumors which comprises administering to the body an effective amount of a compound selected from substantially pure coenzymes $Q_4$ to $Q_{13}$ or mixtures thereof.

10. The method of increasing the survivorship or prolonging the survival time of a body with previously acquired tumors which comprises administering an effective amount of a compound selected from coenzymes $Q_4$ to $Q_{13}$ or mixtures thereof.

11. The method of claim 1, in which the compounds are administered with chloroquine hydochloride.

* * * * *